United States Patent [19]  [11] 4,166,217
Bunnenberg et al.  [45] Aug. 28, 1979

[54] APPARATUS FOR CONTINUOUSLY MEASURING QUANTITATIVE CHANGES IN MOISTURE CONDENSATION AT A SURFACE

[75] Inventors: Claus Bunnenberg; Wilhelm Kühn, both of Hanover, Fed. Rep. of Germany

[73] Assignee: Gesellschaft fur Strahlen- und Umweltforschung mbH Munchen, Neuherberg, Fed. Rep. of Germany

[21] Appl. No.: 840,018

[22] Filed: Oct. 6, 1977

[30] Foreign Application Priority Data

Oct. 6, 1976 [DE] Fed. Rep. of Germany ....... 2644997

[51] Int. Cl.² ........................ G01N 23/00; G01N 5/02
[52] U.S. Cl. ........................................ 250/308; 73/73
[58] Field of Search ................. 250/253, 308, 358; 73/29, 73, 335

[56] References Cited

U.S. PATENT DOCUMENTS 3,243,793  3/1966  Goldman ............................. 250/308

Primary Examiner—Alfred E. Smith
Assistant Examiner—Janice A. Howell
Attorney, Agent, or Firm—Spencer & Kaye

[57] ABSTRACT

Apparatus for the continuous measurement of increases and decreases in moisture condensation at soil and/or plant surfaces, including a dew measuring probe composed of a sample material, a radiation source disposed underneath the probe and emitting beta particles, and a beta particle detector disposed in alignment with the radiation source and on the opposite side of the probe from the source.

10 Claims, 5 Drawing Figures

APPARATUS FOR CONTINUOUSLY MEASURING QUANTITATIVE CHANGES IN MOISTURE CONDENSATION AT A SURFACE

BACKGROUND OF THE INVENTION

The present invention relates to an apparatus for continuously measuring increases and decreases in moisture on ground and/or plant surfaces.

Dew is formed when the temperature falls below the dew point of the atmosphere. The resulting condensed water is then deposited on the surfaces of plants and on ground surfaces. During the heating period following sunrise, the majority of this liquid evaporates again. The quantity of dew formed and its period of dwell on a surface depend essentially on the temperature pattern, surface configuration and water absorption capability of the material constituting the surface. Dew measuring probes should therefore correspond in these characteristics to the natural surfaces and should have as good a contact as possible with the material on which the dew is deposited.

In the dew measuring art there are considered to be basically two types of instruments. The first type relates to instruments which measure the period of dwell of the dew; these instruments do not provide an indication of the quantity of dew, or only provide a very rough indication thereof.

This group of instruments includes the Wallin-Palhemus dew period recorder, the R-2777A precipitation detector, the Crossan and Lemmons-Clark dew recorder, the Stuzka-Uhler apparatus for measuring the moisture on leaves, the Theis-Calpouzos rain and dew recorder, the humectograph, and the Hearn surface moisture recorder.

The other type of instruments, for measuring the dew quantity, includes the Duvdevani dew gauge in which a piece of wood measuring $32 \times 5 \times 2.5$ cm and covered with several layers of a red lacquer presents a surface tension with water such that characteristic drops form when moisture precipitates. The resulting drop configurations are compared with a set of 16 standard drop formers at known precipitation quantities of 0.01 to 0.35 mm. The piece of wood is fastened at sundown to a holder disposed about 1 m above ground. At sunrise the drop formation is evaluated.

There is also known the Potvin dew determination in which the dew is precipitated on a funnel-shaped collector surface and runs into a glass vessel with volume calibrations. The collector surface of this instrument is made of glass while Hungerford-Edgerton and Scott use various plastic materials.

There is also an Ekern weighing lysimeter which is a square box with sides of 150 cm in length and a height of 30 cm which is filled with soil and rests on one side on an abutment. The opposite side is supported by the hydraulic pressure of a water-filled pipe. Dew gain and evaporation losses are indicated by the level of the water in the pipe.

There is also a known dew integrator which includes a measuring element made of a folded cellulose adhesive tape on which the dew precipitates and which is inserted into a modified thermograph. The Hirt-Mac-Dowell surface moisture recorder permits moisture to be deposited on a cylindrical surface of polystyrene. The weight of the cylinder is mechanically transmitted and recorded. In the Kessler-Fuess dew recorder, dew is collected on a slightly conical surface of blackened aluminum. Changes in weight are transmitted mechanically and recorded, while the Hiltner dew scale includes a circular nylon sieve which serves as the dew collecting surface and which is suspened from the balance arm of a scale. Movements of the scale balance are recorded on a writing drum.

A compliation of these dew measuring instruments can be found in the article by T. L. Noffsinger: "Survey of Techniques for Measuring Dew" in HUMIDITY AND MOISTURE, Volume II, edited by A. Wexler.

The first-mentioned type of instrument has the drawback that it merely registers the period during which the dew is present on the surface and does not permit measurements of the quantity of the dew.

Except for the Elkern lysimeter, all other known devices have the drawback that they inaccurately simulate the natural conditions for dew formation and evaporation on soil surfaces. Materials unlike the soil itself serve as collector surfaces and they are not in thermal contact with the soil surface. Some of them do not permit continuous recording. They also measure only the dew formation but not the evaporation.

Other of the known devices make only weight determinations. They have the drawback of being very sensitive to air movements so that the theoretically realizable measuring accuracy of about 0.01 mm precipitation cannot be obtained in practice. Dew formation on the scale balance and on the mount for the collector surfaces produces an additional error.

Only the elkern lysimeter uses natural soil as the collector surface. However, it has a mass of about 1000 kg. If, as has been asserted, 0.025 mm precipitation is measurable, a change in weight of about 60 g should be measurable.

SUMMARY OF THE INVENTION

It is an object of the present invention to continuously measure and record, with high sensitivity and accuracy, the natural dew formation on soil and plant substances as well as the evaporation therefrom, the measured data being available as electrical signals either digitally or in analog form to be processed accordingly.

This and other objects are accomplished according to the present invention by the provision of continuous measurement apparatus composed of a dew measuring probe of a natural soil or plant-like material, a radiation source arranged below the dew measuring probe with respect to the soil surface and emitting beta particles, and a beta particle detector facing the radiation source and located on the opposite side of the dew measuring probe from the radiation source.

According to one feature of the invention, the radiation source is designed as a planar source which may consist of thallium $(Tl)^{204}$.

According to another feature of the invention the dew measuring probe includes a ceramic disc. In this case, the dew measuring probe and radiation source may be accommodated in a dish-type holder.

In further accordance with the present invention, the dish is provided with a recess at its bottom so as to increase contact with the ground.

According to another feature of the invention, the dish is disposed on a stand which can simultaneously by used as a mount for the detector.

In the apparatus according to the invention, the dew measuring probes are thus made of natural soil or a material similar to soil or vegetation. The probes are brought into thermal contact with the surface of the soil or are arranged at the level of the leaves of plants. The remaining structure of the device is also made of material which has a thermal behavior similar to that of the soil.

The high measuring sensitivity is attained through the use of the beta ray adsorption method. The dew-covered sample of material is irradiated by a beta source disposed therebelow. A beta-sensitive detector above the probe measures the intensity of the radiation.

The beta radiator is selected according to known absorption laws so that a change in the weight per unit area of between about 130 mg/cm$^2$ and 230 mg/cm$^2$ produces a maximum change in intensity, i.e. an optimum measurement of precipitation of from 0 to 1 mm is possible on a layer of soil 1 mm in thickness. In the case of greater layer thickness and higher amounts of precipitation, the radiation energy of the radiator must be selected to be correspondingly higher.

The higher measuring accuracy is realized, on the one hand, by the use of a planar source so that one measured point represents the average precipitation value for a surface of the size of the source and, on the other hand, by suitable selection of the source intensity so that with high counting rates the statistical error of the intensity measurement becomes small.

According to a preferred embodiment of the invention employing a Tl$^{204}$ planar source of 2 mCi, a ceramic disc of 1 mm thickness, an Si surface barrier layer counter spaced at a distance of 50 mm and a commercially available electronic counting system with digital output, a minimum quantity of precipitation of 0.0005 mm can be detected in a measuring period of 1 min. On the basis of a double statistical error during pulse counting, there results an uncertainty of $<\pm 0.0002$ mm. An increase in the source intensity or reduction of the distance or lengthening of the measuring period, respectively, permits reduction of the value of the smallest amount of precipitation to be detected as well as of the measuring error.

DESCRIPTION OF THE PREFERRED EMBODIMENTS

Figure 1:
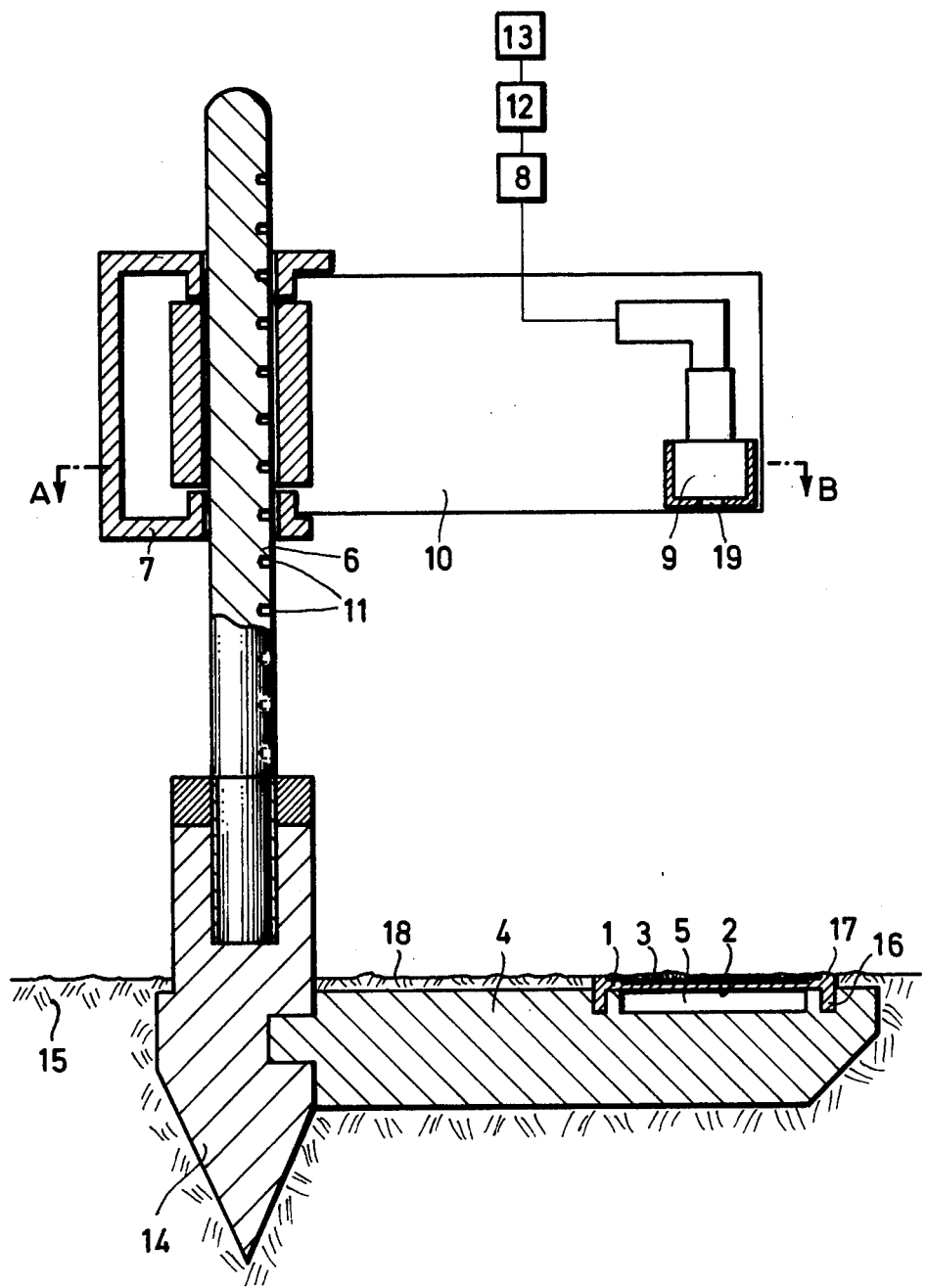
FIG. 1 is an elevational, cross-sectional view of one possible embodiment of a measuring device according to the invention.
Figure 2:
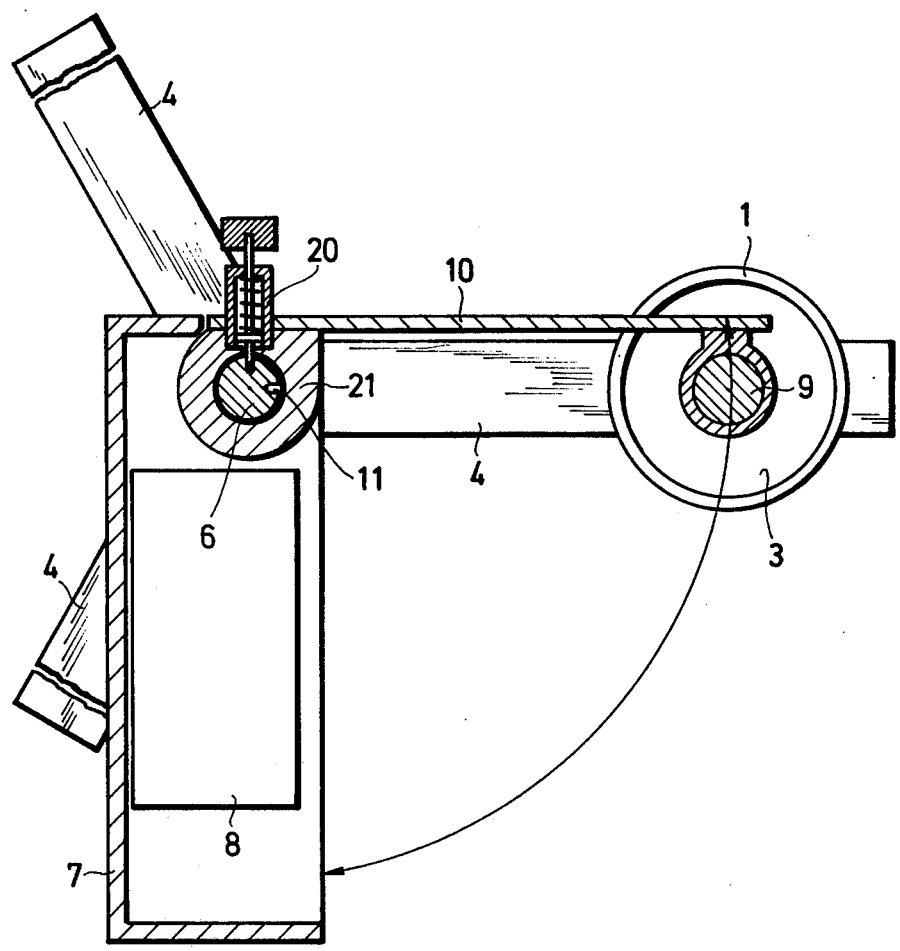
FIG. 2 is a cross-sectional view along the line A–B of FIG. 1.

FIG. 1 shows a measuring device including a supporting rod 6 which can be fastened in the ground 15 by means of a stake 14. Three legs 4 are also buried in the ground 15 at equal distances around the axis of rod 6, as can be seen in FIG. 2 so that good soil contact is provided, and a dish 1 with a lower peripheral edge 16 and an upper peripheral edge 17 is fastened onto one of the legs.

A planar source 2 which includes a beta radiator and which may, for example, be circular, is disposed in the depression formed in the upper surface of dish 1 by edge 17. The upper edge 17 serves as a holder for a disc of a soil or plant-like material or for a corresponding layer of soil 3. Furthermore, edge 17 facilitates leveling and establishment of the desired soil layer thickness when, for example, a soil layer 1 mm thick is to be provided.

A recess 5 in the upper surface of the one leg 4 below dish 1, which recess is enclosed by lower edge 16 of dish 1, provides for contact with the soil for dish 1 over a larger area in that the recess is, for example, filled with soil itself. Supporting rod 6 with feet 4 is forced into the ground 15 to such an extent that the upper surface of the sample 3 and the upper surface 18 of the surrounding soil are flush. To facilitate this, the surface of the soil can be preliminarily pressed down with a ram (not shown in detail) before the device is installed.

A housing 7 which is adjustable and fixable in height is fastened to supporting rod 6 and accommodates the detector preamplifier 8. Housing 7 serves as protection against the weather for detector 9 during periods between measurements. The detector 9 has a beam entrance aperture 19 and is disposed opposite the radiation source and the layer of soil 3.

The detector 9 is attached to the cover 10 of housing 7, the cover being pivotal about the supporting rod 6. Locating bores 11 are arranged to cooperate with a locking pin of a manually operable locking device 20 mounted in a swivel sleeve 21 supporting cover 20, as shown in FIG. 2, to assure that detector 9, 19 always remains arrested over the center of source 2, at any selected height. The preamplifier 8 is connected with measuring and recording devices 12 and 13, which are shown in FIG. 1 only schematically and which are constituted by well-known systems. In order to measure dew on the surfaces of plants, a plant-like sample material is used in place of the layer of soil 3, and the device is set up at the appropriate height.

FIG. 2 again shows the position of the supporting rod 6 and its feet 4 as well as the attachment of dish 1 and the layer of soil 3 on one of the feet 4. Above dish 1, the detector 9 (upper side visible) is disposed at cover 10, which is held in its position via the arresting device 20 and a selected one of the bores 11. Housing 7 is fixed and the cover 40 may be pivoted with the detector 9 through an angle of 90° into the housing 7. This can be effected via swivel joint 21 provided at supporting rod 6. In this position the apparatus is not in use and the locking pin of the locking device 20 locates in the other row of bores on the supporting rod 6.

Figure 3:
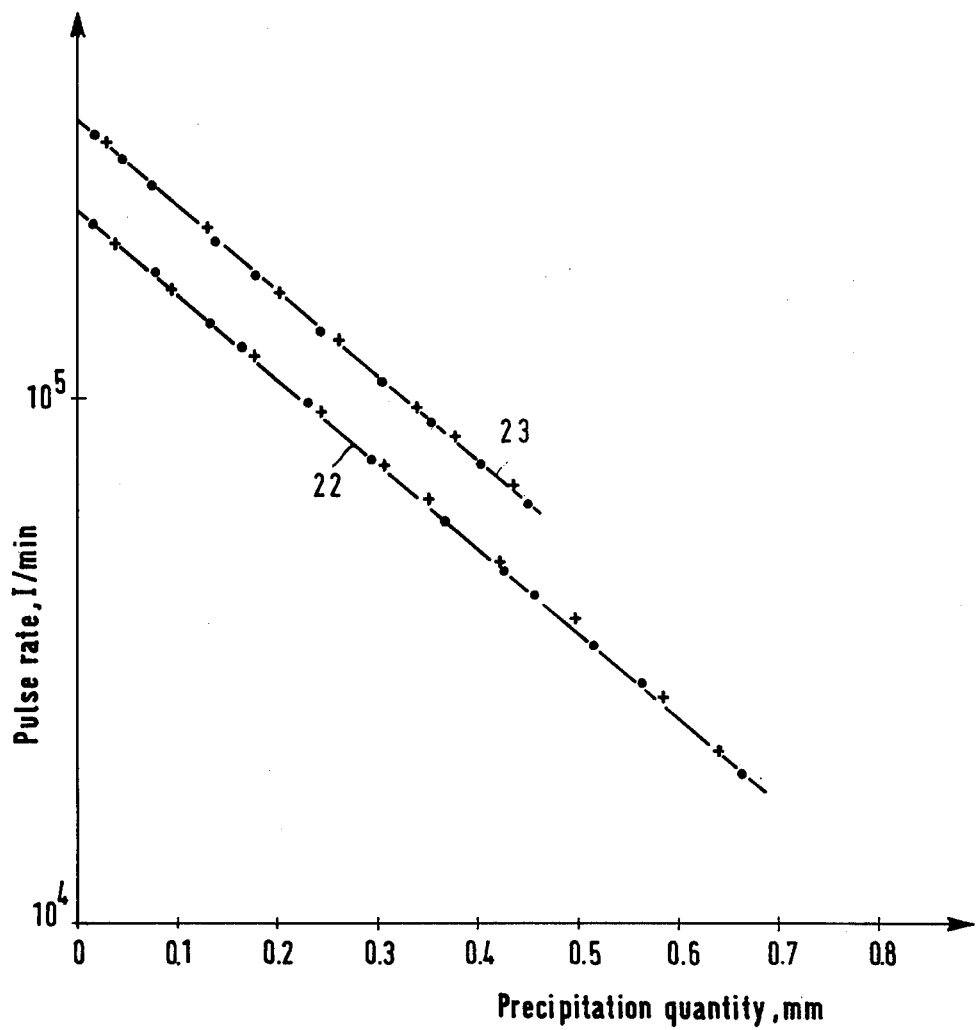
FIG. 3 is a graph showing precipitation calibration curves.

FIG. 3 shows precipitation calibration curves 22 and 23 for 1 mm samples of loess and ceramic, respectively, corresponding to soil layer 3, the dots indicating wetting curve points and the crosses indicating drying curve points. Plotted is the quantity of precipitation in mm, along the abscissa over the counting rate in pulses per minute (I/min), along the ordinate. The relative statistical error is 0.1%. The ceramic material is of the type P25b of the Staatliche Porzellan-Manufaktut, Berlin-West.

Figure 4:
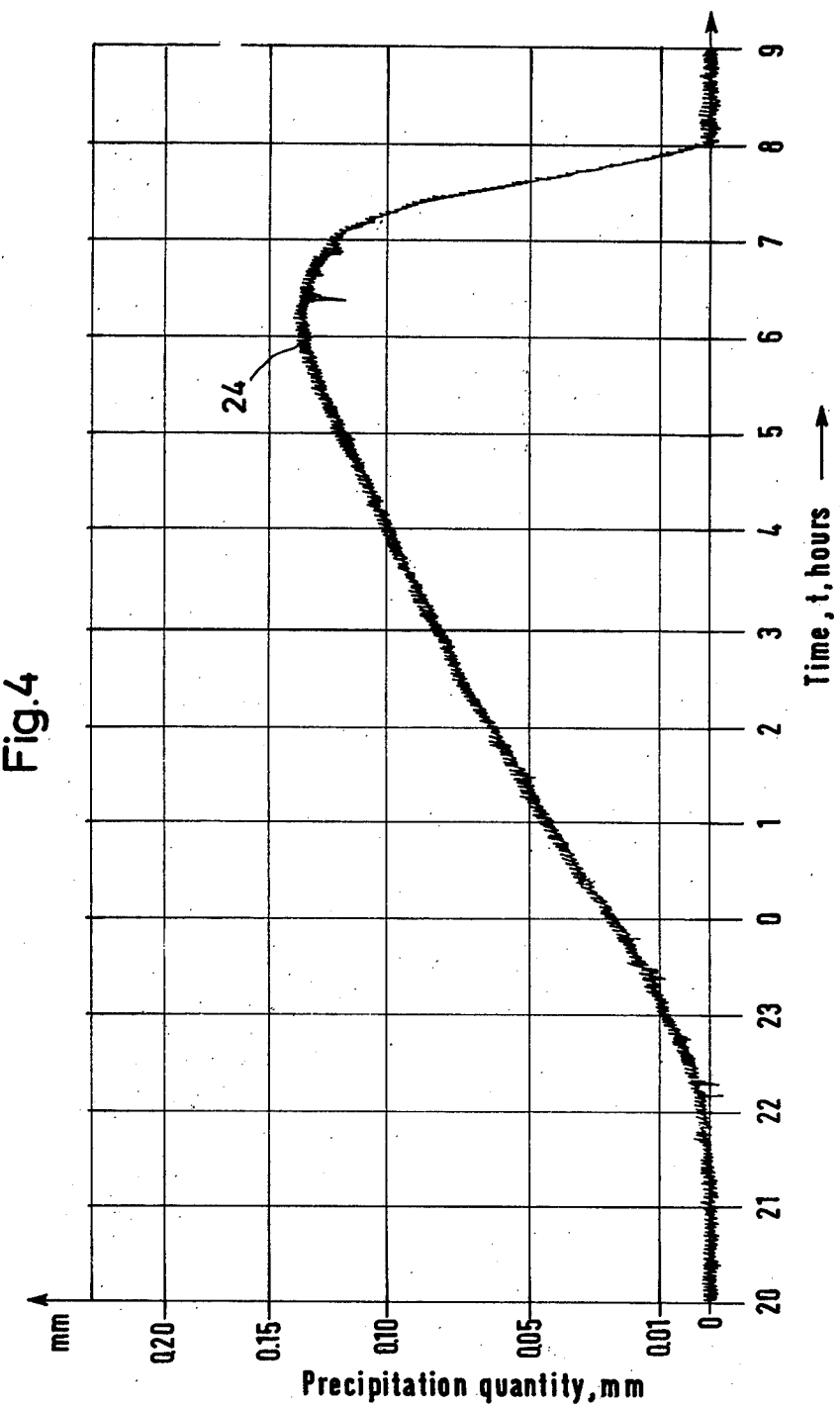
FIGS. 4 and 5 are graphs showing dew formation curves for two different calendar days or nights, respectively.

FIG. 4 shows a precipitation curve 24 which was taken during the night of Aug. 24th to Aug. 25th, 1976, on a meadow in the center of the city of Hannover, Federal Republic of Germany. Plotted is the precipitation in mm as a function of time t, the measurement period extending from 8 PM (20) to 8 AM (8) on the morning of Aug. 25th, 1976. A ceramic disc was used which was placed 9 cm above the ground surface and was provided with a support of a polystyrene foam 6 cm in thickness. This height was selected in such a way that at zero moisture of the probe the recorder shows maximum reading.

Figure 5:
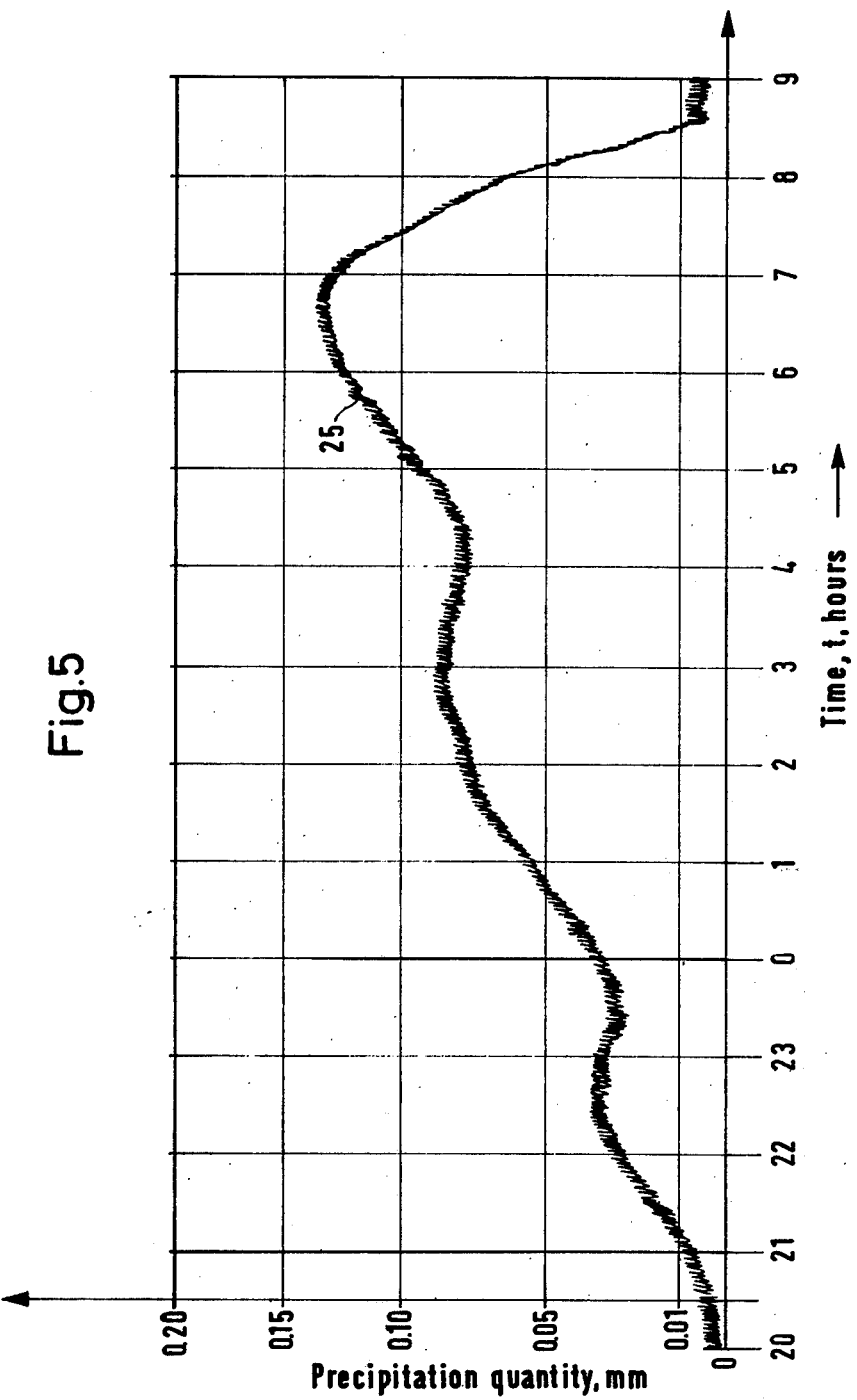

FIG. 5 also shows a recording of precipitation in mm for the period from 8 PM (20) on Aug. 31st, 1976, to 9 AM (9) on Sept. 1st, 1976, recorded on a meadow also in Hannover. Curve 25 clearly shows maxima which indicate that the night was partly cloudy. A ceramic disc was used here as well.

It will be understood that the above description of the present invention is susceptible to various modifications, changes and adaptations, and the same are intended to be comprehended within the meaning and range of equivalents of the appended claims.

What is claimed is:

1. Apparatus for the continuous measurement of increases and decreases in moisture on soil and/or plant surfaces, comprising: a dew measuring probe composed of a sample material; a radiation source disposed underneath said dew measuring probe and constituting means for emitting beta particles; and a beta particle detector disposed in alignment with said radiation source and on the opposite side of said dew measuring probe from said source.

2. An arrangement as defined in claim 1 wherein the sample material corresponds to the material of the surface on which measurement is to be performed.

3. An arrangement as defined in claim 1 further comprising particle counting means connected to said detector.

4. An arrangement as defined in claim 1 wherein said dew measuring probe comprises a ceramic disc.

5. An arrangement as defined in claim 1 wherein said radiation source has a planar form.

6. An arrangement as defined in claim 5 wherein said planar source consists of $Tl^{204}$.

7. An arrangement as defined in claim 5 further comprising a dish serving as a holder accommodating said dew measuring probe and said planar source.

8. An arrangement as defined in claim 7 wherein said dish is provided with a recess in its bottom for increasing contact with the soil.

9. An arrangement as defined in claim 7 further comprising a stand on which said dish is disposed and constituting a mount for said detector.

10. Apparatus for the continuous measurement of the quantity of dew present on a soil and/or plant surface, comprising: means defining a horizontal dew collecting surface composed of a ceramic disc provided with a region for holding a sample material and arranged to be selectively disposed in thermal contact with soil or at the height of such plant surface; a planar beta particle emitting source; and a beta particle detector disposed in alignment with said source; wherein said collecting surface is disposed between said source and said detector and is oriented substantially perpendicular to the path between said source and said detector.

* * * * *